(12) United States Patent
Gordon et al.

(10) Patent No.: US 8,981,135 B2
(45) Date of Patent: Mar. 17, 2015

(54) PROCESS FOR PRODUCING BIODIESEL THROUGH LOWER MOLECULAR WEIGHT ALCOHOL-TARGETED CAVITATION

(71) Applicant: Cavitation Technologies, Inc., Chatsworth, CA (US)

(72) Inventors: Roman Gordon, Studio City, CA (US); Igor Gorodnitsky, Marina del Rey, CA (US); Varvara Grichko, Woodland Hills, CA (US)

(73) Assignee: Cavitation Technologies, Inc., Chatsworth, CA (US)

( * ) Notice: Subject to any disclaimer, the term of this patent is extended or adjusted under 35 U.S.C. 154(b) by 11 days.

(21) Appl. No.: 14/072,156

(22) Filed: Nov. 5, 2013

(65) Prior Publication Data

US 2014/0059922 A1  Mar. 6, 2014

Related U.S. Application Data

(63) Continuation of application No. 12/821,000, filed on Jun. 22, 2010, now Pat. No. 8,603,198.

(51) Int. Cl.
*C11B 3/02* (2006.01)
*C10L 1/18* (2006.01)
(Continued)

(52) U.S. Cl.
CPC .............. *C10L 1/1802* (2013.01); *C07C 67/03* (2013.01); *B01F 5/0644* (2013.01); *B01F 5/0646* (2013.01); *B01F 5/0652* (2013.01); *B01F 5/0653* (2013.01); *B01F 5/0682* (2013.01); *B01F 5/0688* (2013.01); *B01F 13/1025* (2013.01); *B01F 13/1027* (2013.01); *B01J 10/002* (2013.01); *B01J 19/0066* (2013.01);
(Continued)

(58) Field of Classification Search
USPC ......................................................... 554/169
See application file for complete search history.

(56) References Cited

U.S. PATENT DOCUMENTS

| 1,454,196 A | 5/1923 | Trood |
| 1,626,487 A | 4/1927 | Warren |

(Continued)

FOREIGN PATENT DOCUMENTS

| DE | 10310442 A1 | 9/2004 |
| GM | 77 33 456 U1 | 5/1978 |

(Continued)

OTHER PUBLICATIONS

K. Mahesh, G. Constantinescu, P Moin; A numerical method for large-eddy simulation in complex geometries; Journal of Computational Physics; Nov. 19, 2003; pp. 215-240; vol. 197; Elsevier Inc.

(Continued)

*Primary Examiner* — Yate K Cutliff
(74) *Attorney, Agent, or Firm* — Kelly & Kelley, LLP

(57) ABSTRACT

A method for producing fatty acid alkyl esters from biolipids through transesterification and/or esterification reactions uses a flow-through cavitation device for generating cavitation bubbles in a fluidic reaction medium. The fluidic medium is passed through sequential compartments in the cavitation device having varying diameters and inner surface features to create localized reductions in fluid pressure thus vaporizing volatile alcohols and creating an increased surface area and optimized conditions for the reaction to occur at the gas-liquid interface around the bubbles.

11 Claims, 5 Drawing Sheets

(51) Int. Cl.
  *B01F 5/06* (2006.01)
  *B01F 13/10* (2006.01)
  *B01J 10/00* (2006.01)
  *B01J 19/00* (2006.01)
  *B01J 19/24* (2006.01)
  *C10L 1/02* (2006.01)
  *C11B 13/00* (2006.01)
  *C11C 3/00* (2006.01)
  *C07C 67/03* (2006.01)

(52) U.S. Cl.
  CPC ............ *B01J 19/008* (2013.01); *B01J 19/2415* (2013.01); *C10G 2300/1011* (2013.01); *C10L 1/026* (2013.01); *C11B 13/00* (2013.01); *C11C 3/003* (2013.01); *Y02E 50/13* (2013.01)
  USPC ........................................................ 554/169

(56) References Cited

U.S. PATENT DOCUMENTS

| | | | |
|---|---|---|---|
| 3,167,305 A | 1/1965 | Backx et al. | |
| 4,014,961 A | 3/1977 | Popov | |
| 4,213,712 A | 7/1980 | Aanonsen | |
| 4,698,186 A | 10/1987 | Jeromin et al. | |
| 5,302,325 A | 4/1994 | Cheng | |
| 5,492,654 A | 2/1996 | Kozjuk et al. | |
| 5,514,820 A | 5/1996 | Assmann et al. | |
| 5,849,939 A | 12/1998 | Mittelbach et al. | |
| 5,937,906 A | 8/1999 | Kozyuk | |
| 5,969,207 A | 10/1999 | Kozyuk | |
| 5,971,601 A | 10/1999 | Kozyuk | |
| 6,200,486 B1 | 3/2001 | Chahine et al. | |
| 6,227,694 B1 | 5/2001 | Mitake et al. | |
| 6,276,823 B1 | 8/2001 | King | |
| 6,279,653 B1 | 8/2001 | Wegener et al. | |
| 6,440,057 B1 | 8/2002 | Ergun et al. | |
| 6,489,496 B2 | 12/2002 | Barnhorst et al. | |
| 6,502,979 B1 | 1/2003 | Kozyuk | |
| 6,705,396 B1 | 3/2004 | Ivannikov et al. | |
| 6,935,770 B2 | 8/2005 | Schueler | |
| 6,979,757 B2 | 12/2005 | Powers | |
| 7,086,777 B2 | 8/2006 | Kozyuk | |
| 7,207,712 B2 | 4/2007 | Kozyuk | |
| 7,247,244 B2 | 7/2007 | Kozyuk | |
| 7,247,739 B2 | 7/2007 | Gapes et al. | |
| 7,338,551 B2 | 3/2008 | Kozyuk | |
| 2005/0237855 A1 | 10/2005 | Kozyuk | |
| 2006/0063242 A1 | 3/2006 | Chou | |
| 2006/0224005 A1 | 10/2006 | Felly | |
| 2007/0041266 A1 | 2/2007 | Huymann | |
| 2007/0055073 A1 | 3/2007 | McGurk | |
| 2007/0189114 A1 | 8/2007 | Reiner et al. | |
| 2009/0038210 A1 | 2/2009 | Kozyuk et al. | |
| 2009/0043118 A1 | 2/2009 | Kozyuk | |
| 2009/0141585 A1 | 6/2009 | Al-Otaibi | |

FOREIGN PATENT DOCUMENTS

| | | |
|---|---|---|
| JP | 62-221426 A2 | 9/1987 |
| LV | 12900 B | 2/2003 |
| SU | 633576 | 11/1978 |
| SU | 1790438 A3 | 1/1993 |

OTHER PUBLICATIONS

Xiangbin Li, Guoyu Wang, Mindi Zhang, Wei Shyy; Structures of supercavitating multiphase flows; International Journal of Therman Sciences; Nov. 24, 2007; pp. 1263-1275; vol. 47; Elsevier Masson SAS.

FlowMaxx Engineering, Cavitating Venturis, web article, 1 page, www.flowmaxx.com/cavitate.htm, Mar. 2010 USA.

FlowMaxx Engineering, Venturi Flowmeters, web article, 5 pages, www.flowmaxx.com/cavitate.htm, Mar. 2010 USA.

Gogate, P. et al., A review and assessment of hydrodynamic cavitation as a technology for the future, 2005, Ultrasonics Sonochemistry, 12, pp. 21-27.

Kelkar, M.A. et al., Intesificatin of esterification of acids for synthesis of biodiesel using acoustic and hydrodynamic cavitation, Jan. 4, 2008, Ultraxonics Sonochemistry, 15, pp. 188-194.

Li, S. et al., Static Mixers, 2002, Fluent News, vol. XI, Issue 1, pp. (cover, & 12).

Gogate, Parag R. et al., Cavitation: A technology on the horizon, Jul. 10, 2006, Current Science, vol. 91, No. 1, pp. 35-46.

Li, X et al., Structures of supercavitation multiphase flows, 2008, International Journal of Thermal Sciences 48, pp. 1263-1275, Elsevier Masson SAS.

PROCESS FOR PRODUCING BIODIESEL THROUGH LOWER MOLECULAR WEIGHT ALCOHOL-TARGETED CAVITATION

FIELD OF THE INVENTION

The present invention is directed to a method for producing biofuel or biodiesel. More particularly, the present invention is directed to a method for producing such biofuel from biolipid (oil or fat) using a hydrodynamic cavitation, including flow-through cavitation, rotor-stator cavitation and/or high-speed jet collision cavitation to generate alcohol vapor-filled bubbles in a heterogeneous reaction mixture. The present invention is also directed to a method for creating hydrodynamic flow-through cavitation.

The present invention comprises a method for processing heterogeneous and homogeneous liquid systems via a static mechanical device that creates cavitation in a fluidic flow. The cavitation facilitates synthesis of a final product. The method may also find application in other areas of fluid processing and other fields of industry.

BACKGROUND OF THE INVENTION

Biodiesel is fatty acid alkyl esters (for example, methyl or ethyl esters) derived from vegetable oil and animal fat through esterification of fatty acids or transesterification of triglycerides. In such reactions, a low-molecular weight alcohol (in most applications, methanol or ethanol because of the low steric hindrance) is added to a biolipid and the mixture is processed in the presence of a basic or acidic catalyst or lipase. Biolipid transesterification is a three-step process reacting a biolipid with a low-molecular weight alcohol in the presence of a catalyst to convert molecules of said oil or fat to fatty acid alkyl esters and glycerol. Possible low-molecular weight alcohols include methanol, ethanol, 1-propanol, 2-propanol, 1-butanol, etc. Possible catalysts include a hydroxide or alkoxide of sodium, potassium, calcium, barium, an acid or lipase.

A base-catalyzed transesterification involves the nucleophilic attack of alkoxide at the carbonyl group of the triglyceride that generates a tetrahedral intermediate, from which the new ester and the corresponding anion of the diglyceride are evolved, followed by formation of another new ester molecule and monoglyceride anion, etc. The acid-catalyzed transesterification involves the protonation of triglyceride carbonyl group resulting in the formation of carbocation which, after a nucleophilic attack of the alcohol, produces the tetrahedral intermediate, which eliminates glycerol to form the new ester and to regenerate the catalyst H+ (Schuchardta et al., 1998, J. Braz. Chem. Soc. 9: 199-210).

Systems are known in the field, i.e., batch systems, whereby a catalyst (for example, alkaline metal methoxide) is mixed with methanol. The solution is then added to warm oil and the mixture is heated, typically to about 50-60° C. for about 2-12 hours, to allow the transesterification to proceed. Then the mixture is left to stand to allow for separation of biodiesel and glycerol, which may take up to 10 hours. In a continuous biodiesel production process, the reaction mixture is kept at high pressures (over 1,000 psi) within a pressure vessel. In such high-pressure systems, the temperature of oils and fats exceeds 50° C. Such a process requires significant energy input, heavy equipment and a lot of foundation space. In conventional methods, temperature for transesterification conducted at atmospheric pressure is limited by the methanol boiling point (64.7° C.).

In the processes mentioned above, the best approach to making biodiesel is using feedstock with low free fatty acids (FFA) content. High FFA content, in combination with the alkaline metal-catalyzed transesterification, lowers the yield producing soap stock. There are two approaches to FFA removal at different stages of biodiesel production, including: i) caustic stripping (alkali refining) of fat; and ii) a two-step acid-catalyzed esterification/base-catalyzed transesterification treatment. Caustic stripping yields feedstock that can be transesterified to fatty acid alkyl esters but results in saponification and lower yield. The two-step treatment comprises an acid-catalyzed esterification followed by a base-catalyzed transesterification, which produces a higher yield. (A. Demirbaş, 2008, Biodiesel: A Realistic Fuel Alternative For Diesel Engines. Springlert-Verlag London Limited, 205 pp.)

Existing technologies that find application in the processing industries are similar in concept in that they all require an input of energy to produce a final product. For example, some technologies include a pressurized homogenizer, which uses a sequential valve assembly to increase fluid pressure in the material being processed. Such a device requires a large energy input, producing a high outlet pressure, usually in excess of 5,000 psi. Since fatty acid triglycerides and lower alcohols cannot be mixed because of their poor solubility, many patents disclose stirring apparatuses. For example, U.S. Pat. No. 5,514,820 Assmann et al. teaches applying a Reynolds Number exceeding 2,300, and US Patent Application No 2003/10630097 by Hooker teaches ultrasonic cavitation in the reaction section to perform transesterification at or near atmospheric pressure. US Patent Application No 2008/12167516 by Kozyuk discloses a method comprising applying a controlled flow cavitation apparatus to a biodiesel production process in order to increase fatty acid alkyl ester yield.

Cavitation is defined as the generation, subsequent growth and ultimate collapse of vapor- or gas-filled cavities in liquids resulting in significant energy release. As understood in this broad sense, cavitation includes the familiar phenomenon of bubble formation when water is brought to a boil under constant pressure. In engineering and science, the term cavitation is used to describe the formation of vapor-filled cavities in the interior or on the solid boundaries created by a localized pressure reduction produced by the dynamic action of a liquid system.

Cavitation can occur at numerous locations in a fluid body simultaneously and can generate very high localized pressure and temperature (a few thousand atmospheres and a few thousand Kelvin). Cavitation also results in the generation of localized turbulence and liquid micro-circulation, enhancing mass transfer. Thus, mass transfer-limited reactions, endothermic reactions and reactions requiring extreme conditions can be effectively carried out using cavitation. Moreover, radicals generated during cavitation due to the homolytic dissociation of the bonds of molecules trapped in the cavitating bubbles or in the affected surrounding liquid, result in the occurrence of certain reactions.

In homogenous reactions, both the reagents and products remain in the same phase. The mechanical effects of cavitation play a smaller part in such reactions in comparison with the creation of high-energy intermediates. In heterogeneous reactions, cavitation bubbles collapsing at or near the phasic interface causes vigorous mixing. The surface area available for the reaction between the phases is significantly increased, thus improving the rate of reaction.

TABLE 1

Comparison of energy efficiency for different methods.

| Method | Time, min | Yield, % | Yield/energy, $kJ^{-1}$ |
|---|---|---|---|
| Acoustic | 10 | 99 | $8.6 \times 10^{-5}$ |
| Conventional with stirring | 180 | 98 | $2.7 \times 10^{-5}$ |
| Presented flow-through | 8 | 99.9 | $2.6 \times 10^{-3}$ |

It can be seen from Table 1 that reactions that take place in a flow-through cavitation generator are about 30 times and 100 times more efficient compared to acoustic cavitation the agitation/heating/refluxing method, correspondingly.

Accordingly, there is a need for a method to carry out heterogeneous reactions that does not require a large amount of energy input. Further, there is a need for such a method that avoids potentially dangerous, high-pressure operation. The present invention fulfills these needs and provides further related advantages through the utilization of hydrodynamic flow-through cavitation and the chemical and physical reactions and process involved.

SUMMARY OF THE INVENTION

The method described herein does not require high energy input as the cavitation device is static, i.e., it does not contain moving parts. The apparatus simply requires a minimum input fluid velocity and pressure to create cavitation in the flow towards the goal of creating new products.

The inventive process is directed to a method for producing fatty acid alkyl esters through a transesterification of biolipids, i.e. oil or fat. The process begins with mixing a low-molecular weight alcohol with the oils or fats in the presence of a catalyst to form a fluidic reaction medium. The mixture of fatty acid alkyl (usually, methyl or ethyl) esters or other suitable esters comprises a biodiesel fuel. The catalyst comprises an alkoxide, a carbonate or hydroxide of sodium, potassium, calcium or barium, an inorganic base, an organic base, TBATB (tetrabutylammonium tribromide), hydrochloric acid, sulfuric acid, sulfonic acid, heteropoly acid, a Lewis acid, a Brønsted acid, a Brønsted acidic ionic liquid, a membrane catalyst, or an acetyl chloride/ethanol as a source of hydrochloric acid, lipase or other base, acid or enzyme. The heterogeneous catalyst can be bound to the inner surface of the cavitation device, inserts, resin, particles or nanoparticles, including magnetic and carbonaceous particles and nanoparticles, and nanodiamonds. The alcohol comprises a C1-C4 alcohol. The biolipid is crude or preliminarily treated plant oil, including canola oil, castor bean oil, coconut oil, corn oil, cotton oil, hemp oil, jatropha oil, linseed (flax seed) oil, mustard seed oil, nut oil, olive oil, palm oil, peanut oil, rapeseed oil, safflower oil, soybean oil, sunflower oil, tall oil, algal oil, animal fat, including grease, lard, tallow and waste fat, bird fat, fish oil, and any oil produced by using wild-type or genetically modified bacteria, yeast, fungi or other live unicellular or multicellular organisms. In order to avoid the excessive formation of soaps during alkaline metal-catalyzed transesterification, the FFA content of the feedstock should not exceed 5%.

The fluidic medium is introduced into a flow-through static reaction chamber with a pump at an initial fluid pressure. The static reaction chamber has a passageway without moving parts therethrough. The fluidic medium is flowed through the passageway such that any given portion of the fluidic medium passes through the reaction chamber in a matter of seconds or faster. Depending upon the scale of the reaction chamber, the residence time of any given portion of the fluidic medium through the reaction chamber could be anywhere from less than a second to a number of seconds. The fluidic medium is passed through sequential compartments in the passageway that have varying diameters and inner surface features to cause the fluidic medium to undergo localized alterations in pressure.

In a preferred embodiment, the fluidic medium is flowed through sequential compartments of progressively smaller diameter. The progressively smaller diameters decrease the fluid pressure and generate cavitation features in the fluidic medium. The fluidic medium is forced to flow around a baffle body or bodies positioned in the passageway and through narrow openings. Flowing through these parts further decreases the fluid pressure and generates additional cavitation features in the reaction medium. In addition, the fluidic medium may be forced to flow through orifices in a constrictor plate positioned in the passageway such that the fluidic medium flows through multiple orifices. Flowing through these multiple narrow orifices further reduces the fluid pressure and generates even more cavitation in the fluidic medium.

The reduction in the fluid pressure causes the fluidic medium to approach the liquid/vapor pressure threshold for the lowest-boiling point and most volatile reagent(s), i.e., methanol, ethanol and/or other low-molecular weight alcohols that are present in the reaction mixture. Once this liquid/vapor phase pressure threshold is reached, the volatile alcohol in the fluidic medium begins to vaporize in localized areas. This vaporization generates cavitation bubbles in the fluidic medium comprised of the vapors of the volatile alcohol, followed by subsequent localized elevations of pressure and temperature when the bubbles collapse. The localized elevations of pressure and temperature activate the alcohol molecules and drive the transesterification and/or esterification reaction(s) by virtue of reacting gaseous phase alcohol molecules with liquid phase oil/fat molecules. The reaction of the gas-phase alcohol and liquid-phase fatty acid triglycerides proceeds at a fast rate resulting in a higher yield and a lower inhibitory effect of present FFA.

After the cavitation region, the fluidic medium is flowed through a compartment of larger diameter. The larger diameter increases the fluid pressure and restores the pressure to the initial fluid pressure, thus eliminating cavitation features in the reaction mixture.

The produced fatty acid alkyl esters can be separated from the glycerol during the transesterification reaction or after its completion. The separation can be accomplished by using a separator, centrifuge, filtration or by allowing the glycerol to settle out of the reaction mixture through gravitation, by using adsorption, distillation, extraction, suitable reagents or by other means.

In a particularly preferred embodiment, the present invention relates to a method for producing biodiesel from biolipids. The method begins with the step of mixing biolipids with a low-molecular weight alcohol, such as a C1 through C4 (C1-C4) alcohol, and a catalyst to obtain a two phase, liquid-liquid fluidic reaction mixture. This reaction mixture is pumped through a cavitation device at an inlet pump pressure and an inlet fluid velocity. The cavitation device comprises a flow-through hydrodynamic cavitation device, a rotor-stator cavitation device, a high-energy (high-speed) jet collision cavitation device or any combination thereof. When being pumped through the cavitation device, the fluid pressure of the reaction mixture is reduced such that it reaches the vapor pressure of the low-molecular weight alcohol. The pressure and/or velocity of the reaction mixture is manipulated to achieve cavitation.

Cavitation fluid features are generated in the fluidic reaction mixture to obtain a two-phase liquid-gas fluidic reaction mixture containing said biolipids in a liquid state and the low-molecular weight alcohol in a gaseous state. The cavitation fluid features include low-molecular weight alcohol vapor-filled bubbles. These bubbles are then collapsed, resulting in localized elevations of temperature and pressure. During these localized elevations of temperature and pressure, the liquid state biolipids are reacted with the gaseous state low-molecular weight alcohol to produce the biodiesel and a glycerol. The biodiesel is then separated from the glycerol by using gravity separation, centrifugation, filtration, adsorption, absorption, distillation, vaporization and/or extraction.

The pumping, reducing, generating, collapsing and reacting steps may be repeated in a second cavitation device connected in series or parallel with the cavitation device. The reaction mixture may also be exposed to a sonic or ultrasonic irradiation source.

The biolipids preferably comprise: crude or preliminarily treated plant oil, including canola oil, castor bean oil, coconut oil, corn oil, cotton oil, hemp oil, jatropha oil, linseed (flax seed) oil, mustard seed oil, nut oil, olive oil, palm oil, peanut oil, rapeseed oil, safflower oil, soybean oil, sunflower oil, and tall oil; algal oil; fish oil; animal fat, including grease, lard, tallow and waste fat, bird fat; and any oil produced by using wild-type or genetically modified bacteria, yeast, fungi or other live unicellular or multicellular organisms. The low-molecular weight alcohol preferably comprises a C1-C4 alcohol, methanol, ethanol, 1-propanol, 2-propanol, or 1-butanol.

The catalyst may be bound to the inner surfaces of the cavitation device and preferably comprises: an alkoxide, carbonate or hydroxide of sodium, potassium, calcium or barium; an inorganic base; an organic base; tetrabutylammonium tribromide (TBATB); hydrochloric acid; sulfuric acid; sulfonic acid; a heteropoly acid; a Lewis acid; a Brønsted acid; a Brønsted acidic ionic liquid; a membrane catalyst; acetyl chloride/ethanol; and/or lipase. The biodiesel preferably comprises a fatty acid lower alkyl ester.

The reaction mixture may be heated or cooled prior to being pumped through the cavitation device. The biolipids may also be subjected to an initial hydrodynamic cavitation prior to being mixed with the alcohol and catalyst. The biolipids are preferably combined with a reagent prior to being subjected to the initial hydrodynamic cavitation.

The reducing step comprising the step of flowing the fluidic reaction mixture through sequential compartments of progressively smaller cross-sectional area to decrease the fluid pressure and generate cavitation features in the fluidic reaction mixture. The collapsing step comprising the step of flowing the fluidic reaction mixture through sequential compartments of progressively larger cross-sectional area, to increase the fluid pressure and collapse cavitation features in the fluidic reaction mixture.

In an alternate preferred embodiment, the present invention is directed to a process for producing fatty acid alkyl esters from oil or fat through esterification or transesterification reactions. This process begins with mixing said oil or fat with a low-molecular weight alcohol and a catalyst to form a fluidic reaction mixture. This reaction mixture is then pumped through a passageway in a flow-through cavitation device at an inlet pump pressure and an inlet fluid velocity. While being pumped, the fluidic reaction mixture is flowed through the passageway at a flow rate such that any given portion of the fluidic reaction mixture passes through the cavitation device in a few seconds. The fluidic mixture is passed through sequential compartments in the passageway. Each of these sequential compartments have varying diameters and inner surface features.

The fluid pressure of the fluidic reaction mixture is reduced such that it reaches the vapor pressure of the low-molecular weight alcohol. Once the vapor pressure of the alcohol is reached, cavitational fluid features are generated. The cavitational fluid features include low-molecular weight alcohol vapor-filled bubbles, which produce a two-phase liquid-gas fluidic reaction mixture containing said biolipids in a liquid state and the low-molecular weight alcohol in a gaseous state.

The low-molecular weight alcohol vapor-filled bubbles are then collapsed resulting in localized elevations of temperature and pressure in the reaction mixture. The liquid state biolipids are reacted with the gaseous state low-molecular weight alcohol by FFA esterification and/or triglyceride transesterification to produce fatty acid alkyl esters and glycerol. The fluid pressure of the reaction mixture is then restored to the inlet pump pressure to eliminate the cavitation features. Finally, the fatty acid alkyl esters are separated from the glycerol.

Other features and advantages of the present invention will become apparent from the following more detailed description, taken in conjunction with the accompanying drawings, which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

The present invention is directed to a device and method for processing a fluidic reaction mixture via a hydrodynamic cavitation process with the result being the creation of new products. The reaction components inside the apparatus are influenced by pressure impulses and other features of controlled advanced hydrodynamic cavitation. The device and method herein described follows the aforementioned chemical reactions and processes such that the device stimulates cavitation in hydrodynamic liquids to the point where the end result is increased yield and quality of products.

With reference to the attached drawings, FIGS. 1-6, a method and device for the creation of cavitation processes in fluid flows resulting in localized regions of increased pressure, heat release and vigorous mixing to generate changes in fluids are disclosed. The method and device include the use of a flow-through hydrodynamic multi-stage cavitation reactor to promote chemical and physical processes and reactions that occur in a short time and results in new products. Intense localized heat released because of gas compression and microjet formation, which accompany the implosion of cavitation bubbles, excite molecules contained in vapors and in the adjacent layers of surrounding fluid transiently enriched with the high-boiling point ingredient(s), thereby driving chemical reactions and processes.

Figure 1:
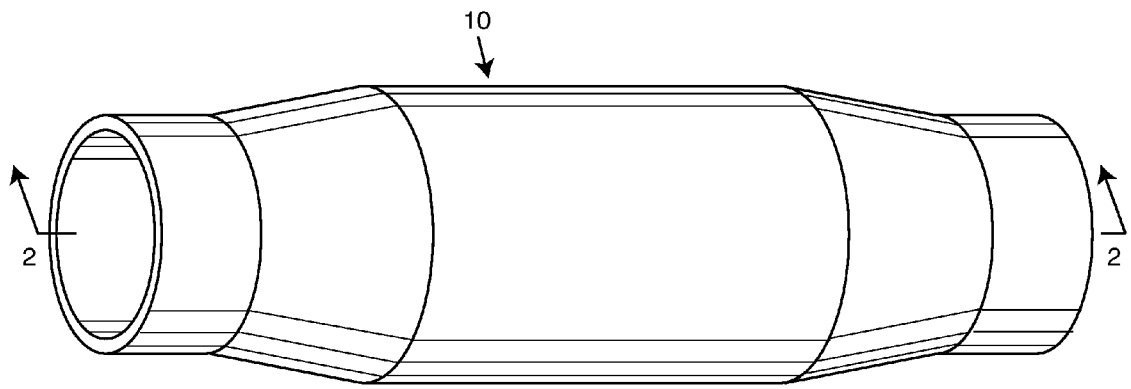
FIG. 1 is a perspective view depicting a preferred embodiment of a multi-stage cavitation device of the present invention.
Figure 2:
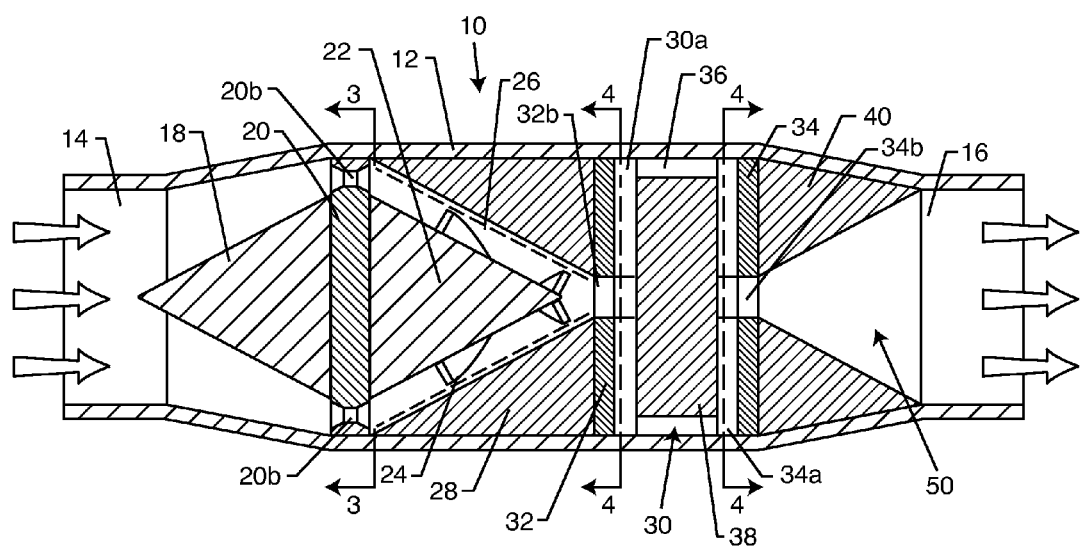
FIG. 2 is a cross-sectional view of the multi-stage cavitation device taken along line 2-2 of FIG. 1.
Figure 3:
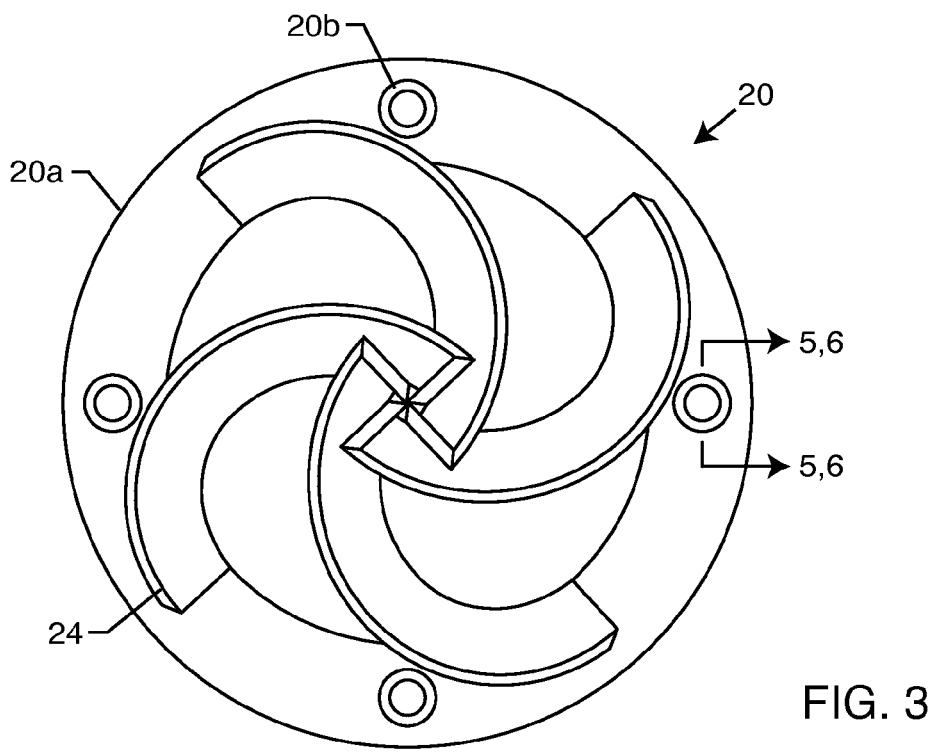
FIG. 3 is a cross-sectional view of the working chamber of the cavitation system taken along line 3-3 in FIG. 2.
Figure 4:
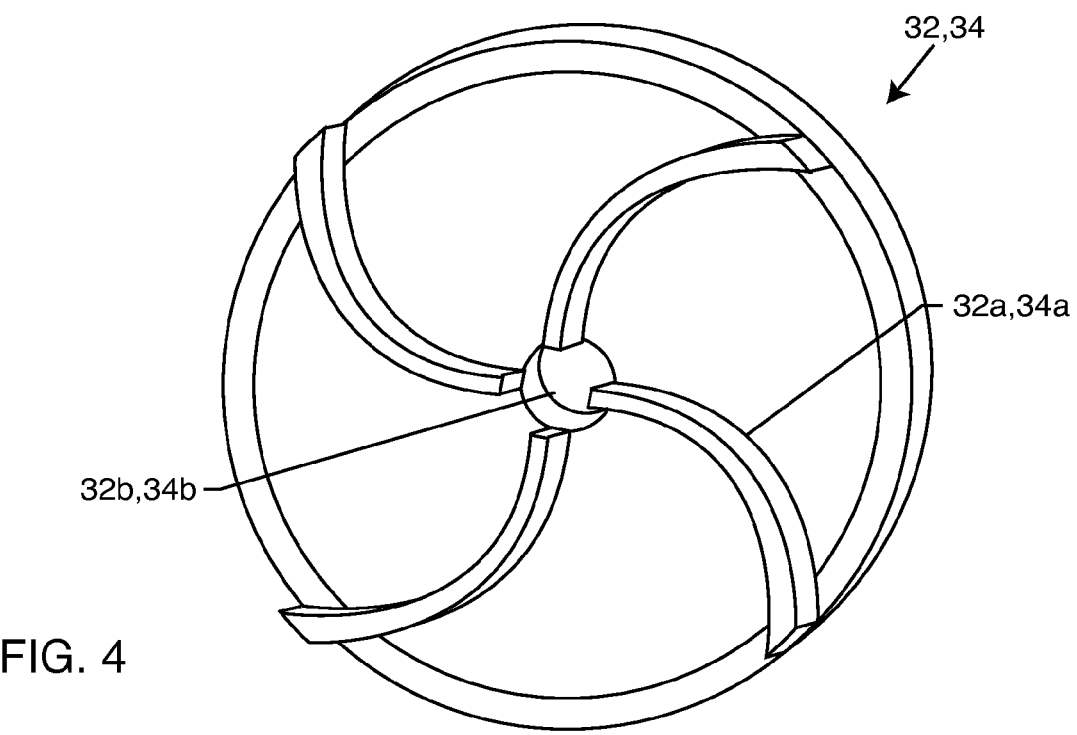
FIG. 4 is a cross-sectional view of the vortex element taken along lines 4-4 in FIG. 2.

A preferred embodiment of the multi-stage cavitation device of the present invention is illustrated in FIGS. 1 and 2, which depict a hydrodynamic flow-through multi-stage cavitation device 10 capable of achieving the objects of the present invention. Said device 10 comprises a housing 12 defining a substantially cylindrical exterior having a fluid inlet 14 and a fluid outlet 16. The fluid inlet 14 is positioned to introduce the fluid medium into the device 10. Between the fluid inlet 14 and the fluid outlet 16 are a series of chambers, as described below, configured to create cavitational features in the fluid medium. The fluid outlet 16 directs the fluid medium from the device 10.

Figure 5:
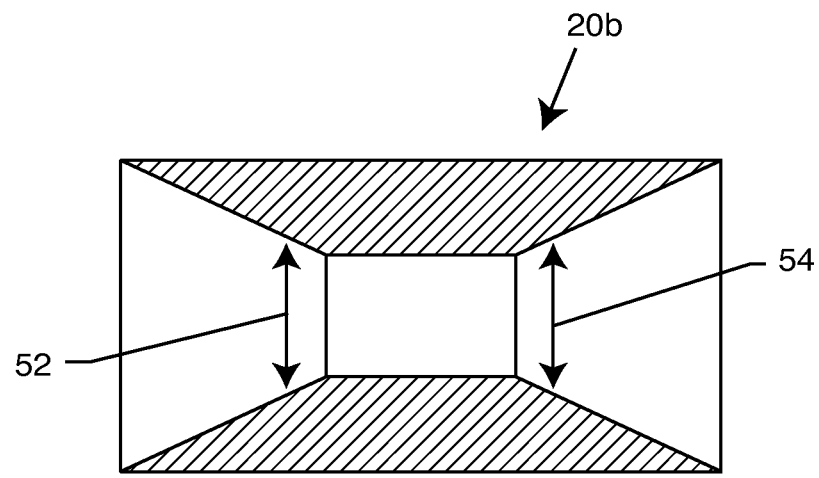
FIG. 5 is a cross-sectional view of one embodiment of a channel in a multi-jet nozzle taken along line 5-5 in FIG. 3.
Figure 6:
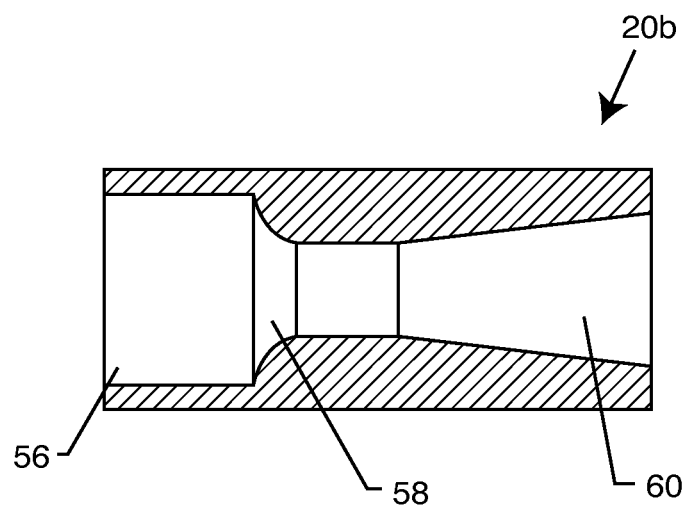
FIG. 6 is a cross-sectional view of an alternate embodiment of a channel in a multi-jet nozzle taken along line 6-6 in FIG. 3.

The cavitation device 10 as shown in FIGS. 1 and 2 is comprised of a cylindrical body 12 made preferably of a metal, an inlet 14 and an outlet 16. An inlet cone 18 is located in front of a multi-jet nozzle 20 along the flow path. A guide cone 22 is positioned behind the nozzle 20 and features spiral guides 24. The multi-jet nozzle 20 is shaped as a disk having a perimeter ring 20a and features four channels 20b that have abrupt contractions and expansions across their width (FIGS. 5 and 6). The number of spiral guides 24 is equal to the number of channels 20b in the multi-jet nozzle 20. The channels 20b are uniformly distributed throughout the surface area of the perimeter ring 20a and direct flow into a working chamber 26.

The working chamber 26 is located behind the multi-jet nozzle 20 along the flow path and has an inner wall formed by the guide cone 22 and an outer wall formed by a convergent cone 28. The convergent cone 28 is aligned coaxially with the guide cone 22. Behind the convergent cone 28 is the vortex chamber or generator 30 comprised of disks 32, 34 with curved flow guides 332a, 34a and central holes 32b, 34b (FIG. 4) that are coaxially aligned. An annular gap 36 is located between the front and rear disks 32, 34 and around a cylinder-type body 38 of slightly smaller diameter than the vortex chamber 30. The curved flow guides 32a, 34a are raised with respect to the disks 32, 34 so as to extend out to the cylinder type body 38. The body 38 blocks the direct path of the fluid flow jet emerging from the central hole 32b in the front disk 32.

The flow guides 32a, 34a create multiple curved flow paths from the central hole 32b in the front disk 32 to the annular gap 36 of the vortex generator 30. Similar paths are created from the annular gap 36 to the central hole 34b on the rear disk 34 on the backside of the cylinder-type body 38. The central holes 32b, 34b, the outlet of the convergent cone 28 and an inlet of an atomizing cone 40, which is situated behind the vortex generator 30 along the flow path, all have the same diameters.

The inventive cavitation device 10 can be made from many materials, although there are some constraints placed on them. The materials should be simple in fabricating and brazing, be able to withstand both high pressure and high temperature, and exhibit high resistance to corrosion, thus allowing the system to be operated continuously and/or repeatedly with a variety of fluids. The materials should be mechanically compatible to assure similar properties of material extension upon heating. A coating with alloys, electrodeposited layer(s), plastics, nanoparticles, nanodiamond, metals, catalysts and enzymes is possible. In one preferred embodiment of the invention, the device is made from a hardened stainless steel.

Both the inner and outer system dimensions depend upon the intended use of the device. A small-scale cavitation system is preferable when the amount of fluid to be processed is limited or its cost is too high. A large system with an inner diameter of ten inches or greater provides a high treatment throughput and may generate larger cavitation features. In the preferred embodiment, the cavitation device 10 is about fourteen inches long with an outside diameter of about three inches.

The present cavitation system provides at least three major cavitation zones and operates as follows. Presumably sufficient fluid is initially pressurized with a proper pressure pump and introduced through the inlet 14 which has a uniform outside diameter of one and one-half inches in the preferred embodiment. The fluidic reaction mixture enters at the top of the inlet cone 18, which is surrounded by the inner peripheral wall of the housing 12. The fluid accelerates over the inlet cone 18 and moves into the channels 20b of the multi-jet nozzle 20. To enhance mixing and cavitation, the channels 20b of the multi-jet nozzle 20 are uniquely shaped and contain both contractions 52 and expansions 54. More particularly, the cross-sectional diameters of the channels 20b vary along the fluid path, as illustrated in FIG. 5.

As illustrated in FIG. 6, the channels 20b can alternately be fabricated as Venturi nozzles to separate vortices and generate pressure pulsations at characteristic frequencies. A Venturi nozzle is defined as a throttle device comprised of a conical inlet 56 with a round profile, a cylindrical throat 58 and a conical outlet (diffusor) 60. The Venturi nozzle generates unsteady flow that can be calculated (Fedotkin and Gulyi, 2000; Mahesh et al., 2004; Li et al., 2008).

When fluid moves through the channels 20b, the vortices, completely detached jets and possible cavitation are produced. They act upon the fluid by altering its properties. The streams exiting adjacent channels 20b are mixed by passing through the narrow gaps formed by the spiral guides 24 mounted between the guide cone 22 and the walls of the convergent cone 28, and flowing through the working chamber 26.

Although this configuration is preferred, it should be understood that the spiral guides 24 do not have to be mounted at a specific angle or at a specific location relative to the channels 20b in order to generate cavitation within working chamber 26. The preferred configuration of the guides 24 has a gradual decrease in the pitch of the spiral toward the peak of the guide cone 22 in order to accelerate the flow velocity. This allows the fluid to form patterns and jets in the flow and form vortices and shear when the flow's upper layers separate from those lying underneath because of the substantial difference in the velocities.

The fluid directed by the guides 24 exhibits significant cavitation within the working chamber 26. Implosion of the generated cavities results in the formation of shock waves, high-velocity local jets and heat dissipation, improving both reaction rates and mass transfer. The jet velocities and intensity of the vortices and cavitation depend on the interaction of a fluid-vapor mixture with vapor. As the cavitation number decreases, fluctuating cavities with periodic vortex shedding, fluid-vapor filled cavities within a turbulent wake, and cavities filled with vapor are observed. In the cavitation region, strong momentum transfer between the higher and lower flow layers occurs. In the core zone of the region, the flow velocity is high and evenly distributed. The low velocity region lessens as the flow path moves downstream. The cavitation bubble dimensions and the intensity of the cavitation field increase as the fluid moves toward the middle part of the working chamber 26. An increase in the difference in flow pressures favors cavitation and vortex formation.

The cross-sectional area of the working chamber 26 decreases along the flow path due to the decrease in diameter of the guide cone 22, and the corresponding diameter of the convergent cone 28 resulting in acceleration of the fluid flow. With the increase in velocity the fluid pressure drops, favoring conditions suitable for cavitation. Moreover, upon exiting the working chamber 26, the fluid is further accelerated by sliding over the spiral guides 24. The fluid then passes into the vortex chamber 30 through the central hole 32b in the front disk 32, enters the flow guides 32b and passes to the annular gap 36. The fluid then follows the flow guides 34a of the rear disk 34 to the central hole 34b. The drastic increase in the cross-sectional area of the flow path, sharp changes of the flow direction and vigorous vortex formation promote nucleation, growth and coalescence of cavitation features. In the vortex chamber 30, the cavitation bubbles are subjected to the increased pressure caused by flow dynamics, i.e., apparent centrifugal and Coriolis forces. Consequently, the bubbles implode at a higher flow velocity than normal.

Near exiting the vortex chamber 30, the fluid, which has been heated by the cavitation process, enters the channels formed by the guides 34a and accelerates due to the narrowing cross-sectional area. When fluid moves along the curved channels, it causes rolling friction, which requires much less force to overcome than sliding friction. The flow guides 32a, 34a of the disks 32, 34 of the vortex generator 30 are shaped as curved arcs of circles in order to reduce the energy required to direct fluid in the vortex generator 30. The energy required to force flow along the convex section of the curved guides 32a, 34a is much less than with straight guides. The force required for overcoming the rolling friction on the concave section of the guides 32a, 34a depends on their curvature.

The vortex flow exits the central hole 34b in the rear disk 34 and atomizes within the cone 40. The drastic increase in cross-sectional area, sharp alterations of the flow direction and its vortex nature promote formation and expansion of cavitation features and other effects. In the outlet 16 from the atomizer 50, the flow rate drops with minimal energy loss until it reaches the level acceptable by the downstream pipe line safety requirements. As the hydrostatic pressure rises, the cavitation bubbles quickly collapse and the negative impact of cavitation on the downstream pipe line and equipment promptly disappear. The flow-through cavitation process may be coupled with UV-Vis-IR light treatments to improve efficiency. The fluid may also be irradiated with sound or ultrasound waves prior to, during and/or after the flow-through cavitation treatment.

The present multi-stage cavitation device 10 provides at least three zones where vigorous vortex formation and intense cavitation occur. The first cavitation zone is within the working chamber 26, the second cavitation zone is in the vortex generator 30, and the third cavitation zone is in the atomizing cone 40. This configuration is particularly cost efficient in a large volume treatment. However, the same principles can be applied to any alteration at smaller scale. Note, that ultrasonic radiation generating devices are not sufficient to induce uniform cavitation in large vessels.

The device 10 schematically presented in FIGS. 1-6 is used for carrying out the method, according to the present invention. In accordance with the present invention, a fluidic reaction mixture is treated either continuously or periodically, by passing through the multi-stage cavitation device 10. The device 10 can be placed anywhere in a production site or any other body. Another design exists in which the device 10 may be fixed in position or movable. In addition, multiple devices 10 may be combined in a series or parallel configuration. In practice, it is necessary to take into account the cost of the device 10, its production capacity and the energy, maintenance and operation cost. It should be emphasized, that an operator of the cavitation device 10 is not required to wear high performance safety products for hearing protection, such as earmuffs or earplugs, as it would be in the case of high-frequency cavitation.

The cavitation device 10 is static, i.e., contains no moving parts, and is configured for operation at a set fluid velocity and pressure of fluid medium. As described below, the changing of chamber diameters and surface features within the device 10 causes the generation of cavitation fluid features, i.e., bubbles. The subsequent collapse of the cavitation bubbles results in the localized elevations of pressure and temperature and drives the transesterification reaction at a higher rate to achieve a higher yield than other processes.

When fluid is subjected to the consecutive multi-stage cavitations it is heated up and becomes enriched with bubble nuclei. This lowers the downstream cavitation threshold, intensifies processing and allows selective chemical reactions to occur while targeting compounds of interest. This makes the present device unique and especially suitable for treatment of multi-component fluids such as, for example, mixtures of low-boiling point alcohols, catalysts and biolipids.

The flow-through cavitation device 10 is a multi-stage apparatus whereby reaction components are manipulated through localized high pressure and temperature impulses and advanced gas phase/liquid phase transesterification reaction principles. Hydrodynamic cavitation assumes formation of vapor bubbles within a fluid accelerated to a proper velocity. In practice, cavitation is achieved by forcing fluids into the flow-through hydrodynamic cavitation device 10 accelerated with a high-pressure pump and/or by reducing the available flow cross-sectional area at constant pressure. The faster the flow rate, the lower the cavitation number. A lower cavitation number (especially cavitation numbers less than 1) equates to a higher degree of cavitation. The preferred embodiment of the present invention optimizes the cavitation to achieve the high reaction yield by applying the most suitable pump pressure selected from a preferred range of 25-5,000 psi. If too much energy is applied or the treatment time is too long, then the cost goes up. By applying hydrodynamic cavitation at a pump pressure designed to cause alcohol-filled bubble formation and chemical conversion consistently throughout the fluidic reaction mixture, proper changes take place and a desirable outcome is achieved.

The present invention uses energy released upon the implosion of cavitation bubbles to carry out transesterification and/or esterification. Hydrodynamic cavitation is the phenomenon of the formation of vapor cavities in a flow of fluid, which is followed by the bubble collapse in a downstream high-pressure zone. In practice, the process is carried out as follows. The fluid flow is fed into the inlet passage 14 of the cavitation device 10. In a cavitation zone 26, 30, 50, the flow accelerates causing the pressure to drop. This pressure drop results in the formation of bubbles filled with the vapors of volatile compounds that boil under the given conditions. When the cavitation bubbles move beyond the boundary of the low-pressure zone, the pressure in the flow increases and the bubbles collapse, exposing the vapors found within them and the surrounding liquid layer to localized high pressure and temperature, shearing forces, shock waves, acoustic vibration and electromagnetic irradiation. Each cavitation bubble serves as an independent mini-reactor, in which chemical reactions occur, particularly at the vapor/liquid interface. The localized pressure and temperature are significantly higher than those found in many other industrial processes where the overall pressure and/or temperature may be increased rather than on a localized scale. The alteration of fluid composition results from the chemical reactions taking place within the collapsing bubbles and/or in the adjacent layers of fluid.

The phenomenon is named cavitation, because cavities form when the fluid pressure has been reduced to its vapor pressure. The vapor bubbles expand as they move and suddenly collapse, creating a region of high pressure. The occurrence of cavitation bubble implosion is accompanied by the formation of numerous deformed micro bubbles. The pressure and temperature of vapors contained in these bubbles are very high. As fluid enriched with these micro bubbles moves into a reduced pressure zone, the micro bubbles become nuclei, which are less stable than those originally present in the fluid, and expand. The cavitation bubbles developed from these nuclei enhance the cavitation field intensity. The continuous process of bubble multiplication, expansion and implosion lowers the cavitation threshold because cavitation bubbles grow from the vapor nuclei, whose volume is larger than that of the naturally present nuclei. The sudden collapse causes tremendous localized increases in pressure and temperature and intense shearing forces, resulting in high yield chemical reactions. By subjecting the fluidic reaction mixture to hydrodynamic cavitation, reagent molecules are activated and are converted into new products.

The fluid directed through the generator 10 exhibits significant cavitation. The cavitation features created in the fluid flow include vapor bubbles of volatile alcohols such as methanol or ethanol. As the velocity of fluid flow increases, its pressure drops. As the fluid pressure drops below the vapor pressure of volatile compounds, those compounds form vapor bubbles. Those of ordinary skill in the art understand that lower molecular weight alcohols have boiling points significantly lower than the boiling points of other reactants such as plant oils, animal fats, glycerol or other compounds that may initially be present or produced in the course of esterification or transesterification reactions. Given these significantly lower boiling points, the alcohols will more readily form vapor bubbles at the reduced fluid pressures in the cavitation device 10 than other non-volatile compounds.

Those skilled in the art are aware that notwithstanding the given pressure there are the huge differences between the boiling points of methanol (64.7° C.) or ethanol (78.4° C.) and those of the reaction products such as glycerol (290° C.) and water (100° C.), and original plant oil or animal fats. The boiling point of oil depends on its composition/purity and is difficult to determine with any precision because oil smokes—decomposing before reaching the boiling point. For example, the smoke points of palm oil, corn oil, and soybean oil are 235, 246 and 257° C., correspondingly. Linoleic acid and oleic acid, which are abundant in oils and fat and boil at 229 and 360° C., respectively. The primary products of the transeterification reaction—fatty acid alcohol esters—boil at a significantly higher temperature compared to methanol or ethanol (see ASTM WK13125—New Determination of Boiling Point Distribution of Fatty Acid Methyl Esters (FAME) in the Boiling Range of 100-615° C. by Gas Chromatography).

The processing is dependant upon the physical properties of the fluid being processed and the energy requirements based upon ambient conditions necessary to generate cavitation in the fluid. It is well known that the complex liquid mixture comprised of different chemical compounds can be separated into pure fractions by heating it to the temperature at which the individual fractions will evaporate (the procedure is called atmospheric fractionation distillation). Generally, the compounds can be efficiently separated by the fractionation distillation at a pressure of 1 atm, if the difference in their boiling points is at least 25° C. Thus, there is no doubt that lower molecular weight alcohols, for example methanol, will boil first under the conditions described in the proposed invention. These first boiling alcohols form bubbles filled with alcohol vapors for providing increased contact area between the liquid oil and the gaseous alcohol for an improved reaction.

The gas-liquid hydrodynamic cavitation-assisted transesterification and/or esterification of the claimed invention begins with an alcohol/oil two-phase, liquid-liquid system. When undergoing cavitation, this liquid-liquid system converts to a gas-liquid system as described. After the transesterification/esterification reaction and the cessation of cavitation, the gas-liquid system reverts to a two-phase, liquid-liquid system comprised of biodiesel and glycerol. The reaction of the claimed method is not affected by transport limitations, as are prior art transesterification reactions due to the radial and axial mixing. This lack of transport limitation and the high-energy alcohol state results in an almost instantaneous reaction and short residence time, i.e., less than about ten seconds and a high yield for the fluid flow processed with the cavitation device 10.

Implosion of the generated cavities results in the formation of shock waves, high-velocity local jets and heat dissipation, improving both mass transfer and reaction rate. As the cavitation number decreases, fluctuating cavities with periodic vortex shedding and vapor-filled cavities are observed. In the cavitation regions, strong momentum transfer between higher and lower flow layers occurs. The cavitation bubble dimensions and the intensity of the cavitation field increase as the fluid moves through the cavitation device 10. An increase in the difference in the flow pressures favors cavitation and vortex formation.

In the case of a cavitation treatment of a multi-component fluid, the composition of the cavitation bubbles differs from that of the fluid. The bubble composition is enriched with the vapors of the compounds that are volatile under the given conditions. The bubble implosion releases energy that drives chemical reactions and/or heats the fluid. The processed mixture contains the products of these reactions, i.e., the newly formed compounds. The size of cavities depends on the nature of the fluid under treatment, the engineering design of the cavitation device, and other conditions, such as the velocity of flow sustained by a pump. The pump pressure may be increased, as determined on a case-by-case basis, until a proper intensity of cavitation is achieved. In addition to determining the size, concentration and composition of the bubbles, and, as a consequence, the amount of energy released, the inlet pressure and device design govern the reaction outcome.

A practical approach to achieve the desired degree of cavitation is to establish a pressure that provides enough bubble implosion energy for mixing and carrying out the reactions.

The optimal pressures produce bubbles in sufficient quantities to achieve a high yield. However, as one skilled in the art understands, different reaction mixtures require different energies obtained through cavitation in order for their products to form. Energy released because of bubble implosion during a flow-through hydrodynamic cavitation process activates molecules forcing them to react and form new compounds.

From an overall point of view, esterification and transesterification in the cavitation apparatus 10 occur at ambient temperature and ambient pressure. No pre-agitation is required. The cavitation-assisted reaction is run at pump pressures between 25-5,000 psi, ideally at around 500 psi. Water in the alkaline metal-catalyzed process promotes saponification and consumes the catalyst, inhibiting the reaction. Thus, precautions have to be taken to eliminate water from the reaction mixture, for example, by using dry reagents or placing water absorbents within the device.

The cavitation apparatus 10 creates conditions for an instant process due to the high-energy state of the gas-phase alcohol molecules, vigorous mixing and the high reactivity of heated liquid-phase biolipids. The biolipid transesterification and FFA esterification is completed in seconds or even faster than that after a single pass through the cavitation device 10, although multiple passes are possible, and biodiesel is produced immediately. It has been observed that 95% conversion in the transesterification reaction can be achieved in a matter of seconds with the claimed method in the presence of a small excess of methanol and about 5% FFA at a temperature ca. 20° C. Complete separation of biodiesel and glycerol can be achieved within minutes via gravitational sedimentation and much faster via centrifuging.

It is important to note that the method of the claimed invention is designed to operate in a manner similar to a plug flow reactor as the fluid flow is pumped through the cavitation device 10. Most prior art disclosures cavitation systems that comprise batch or hybrid batch/continuous systems. In such prior art systems, the reagents are introduced to the system and the reaction is allowed to proceed to equilibrium in a residence chamber/vat. Once equilibrium is achieved, a portion of the products are removed from the system so that the remaining reagents and any subsequently added reagents may react to establish a new equilibrium. Such prior art processes require a long residence time, in some cases many hours, in order to produce the desired yield.

This is especially important in esterification and transesterification reactions since such are reversible. The higher the concentration of products, i.e., fatty acid alkyl esters and glycerol, the slower the rate of transesterification. The rate of the irreversible competing saponification reaction depends on the reactant concentrations. Some prior art systems improved transesterification yield over saponification yield by the continuous removal of the glycerol from the reactor. Although the rate of the saponification reaction slows due to consumption of the reactants by the transesterification reaction, the rate of transesterification slows down as well. This makes the prior art method time consuming, expensive, and less efficient when compared to the claimed method with a near instantaneous transesterification reaction to a high-yield equilibrium.

Further, the prior art methods disclose a transesterification method wherein all reactants are present in the liquid phase. In contrast, the generation of cavitation features in the claimed method results in the formation of transient gas bubbles comprised of methanol, ethanol and/or other low molecular weight C1-C4 alcohols to react with the catalyst-enriched triglycerides being in a liquid phase. This gas-liquid reaction produces a faster and greater yield over the liquid-liquid reaction of the prior art systems. The inventors are not aware of any preexisting teaching or disclosure of a gas-liquid transesterification process for the production of biodiesel fuel. The gas-liquid interface at the surface of each alcohol vapor-filled micro bubble provides a very large interphase reaction surface, superior mixing, and allows for the prompt separation of products into two phases.

While processing vegetable oils, yellow grease, tallow and other animal fats (with less than 5% FFA) with necessary components in the flow-through cavitation device 10, alcohol-filled bubble explosions result in instant reaction, high yield, fast glycerol separation, and improvement of the biodiesel quality. The inventive cavitation device 10 also increases the effectiveness of catalysts used in the reaction, as well as, the rate and efficiency of the reaction.

The present invention makes it possible to carry out accelerated cavitation-assisted esterification and transesterification reactions by causing bubbles to collapse. The invention also allows for the production of biodiesel without consuming large amounts of energy and avoids high-pressure operation. The present invention can produce biodiesel using biolipids with FFA content as high as 5% and phosphorus as high as 250 ppm. This lowers the feedstock pre-treatment cost and prevents the formation of emulsions simplifying the separation of the biodiesel and glycerol products.

One should monitor the concentration of water and FFA in the biolipids be used in the inventive process. If water and FFA levels are too high, it may lower yield and cause excessive soap formation. The separated glycerol may contain high levels of soap that makes it difficult to produce a high-grade glycerol.

Data analysis shows that esterification and transesterification reactions are accelerated by processing with the inventive cavitation device 10, which also decreases the amount of catalyst. Decreasing the amount of base catalyst lowers soap formation.

An alternate embodiment, illustrated in FIGS. 8 to 11, presents a cavitation device 10' made of stainless steel and having a generally cylindrical shape. It is assembled of at least three parts and is provided with threads at the outer surfaces of the inlet and outlet ends for installation in line. Fluidic mixture is fed in to the cavitation device 10' with a pump operating at the pressure that allows sustaining the selective generation of cavitation bubbles composed of alcohol vapors. The fluidic mixture flows through a first cylindrical passage 86 and enters a short downstream cylindrical passageway 88 having a smaller diameter and connected to the first cylindrical passage 86 with a conical opening 90. The fluid flow then enters third and fourth cylindrical passages 92, 94 of progressively larger diameters.

The fourth cylindrical passage 94 has two cylindrical passage openings 96 in its wall each interconnected to an inverted conical passageway 98. In addition, the fourth cylindrical passage 94 is provided with a downstream cylindrical impact pad 100 that has four segments of circumferential wall 102 on its top surface. (FIGS. 10 and 11) The fourth cylindrical passage 94 and impact pad 100 are surrounded by an outer housing 104 that creates an annular chamber 106. The gaps 108 between the wall segments 102 on the top surface of the impact pad 100 connect the annular chamber 106 to an outlet chamber 110. The fluid flow exhibits turbulence when it encounters the bottom surface of the impact pad 100, accelerates passing through the two small openings 96 in the wall of the fourth cylindrical passageway 94, entering annular chamber 106. The fluid flow then moves through annular chamber 106 towards the gaps 108 located between the four segments of the circumferential wall 102 on the top surface of the impact pad 100 where the high-energy jets collide and enter the outlet chamber 110 with a diameter that is smaller than the diameter of the fourth cylindrical passage 94. As the fluidic mixture of biolipid, low molecular weight alcohol and catalyst moves along the passageways of the cavitation device 10', it undergoes multiple cavitation events due to selective alcohol vaporization and subsequent bubble implosion.

One liter of feedstock (60% poultry fat and 40% tallow with 1.8% FFA) was transesterified in device 10' using as low as 17% v/v of methanol (much less when compared to minimal 100% excess in the conventional methods). The separation of biodiesel and glycerol was observed in 15 min after completing the methanol-targeted cavitation; the yield was ca. 99%. It should be noted that with poultry fat containing 0.1% and 2.3% FFA conventional method affords 90 and 70% yield, correspondingly. The inventive method is characterized with 97% yield in a case of poultry fat with up to 2.5% FFA or tallow with the same FFA level. With 2.5-3.5% FFA, the average yield is 95%. With vegetable oil containing less than 2% FFA, the transesterification yield reaches 100%. It should be emphasized that full conversion can be achieved in a matter of seconds by applying the proposed method in the presence of low methanol excess and ca. 5% FFA at the ambient temperature.

Figure 7:
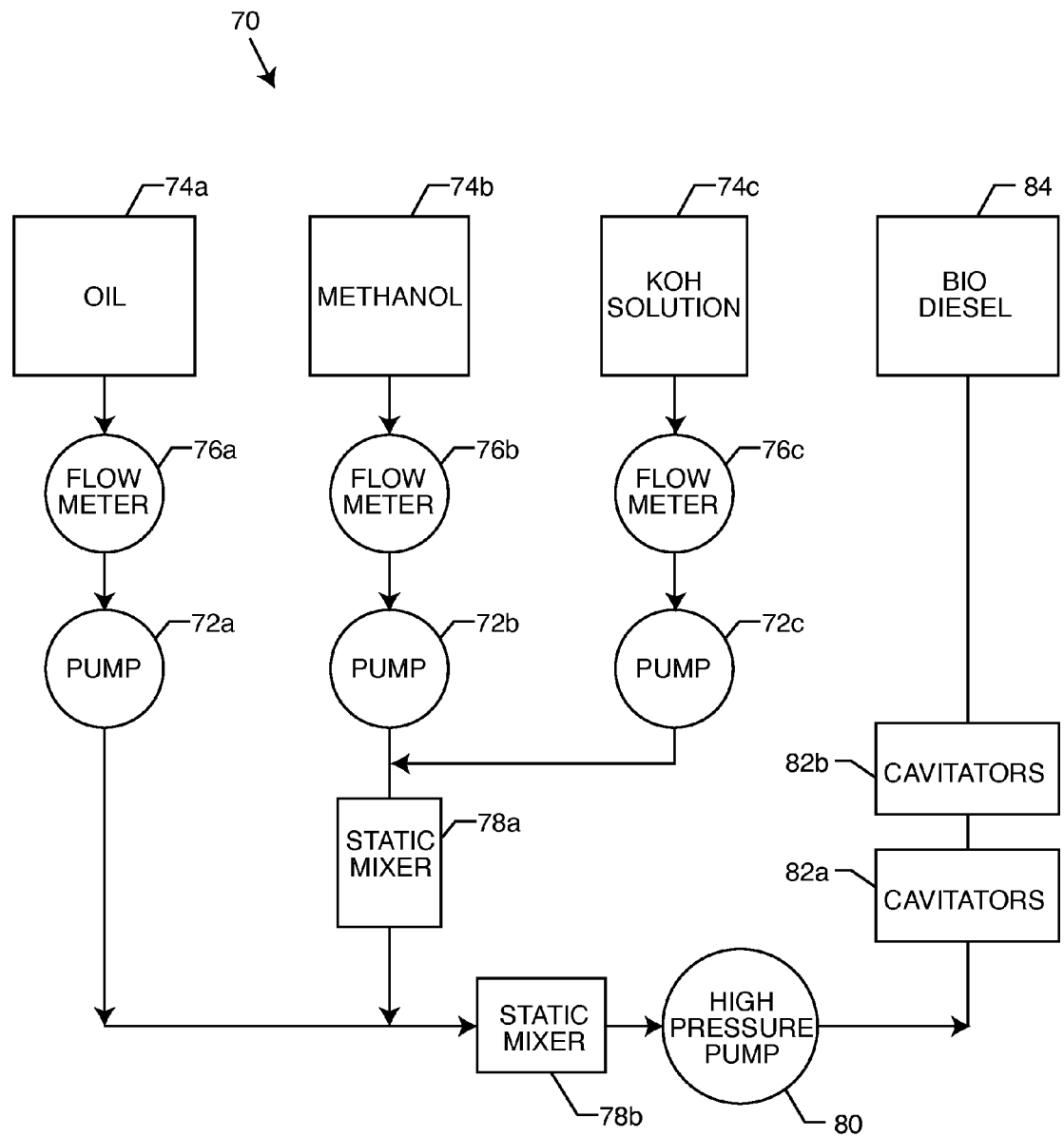
FIG. 7 is a schematic diagram illustrating a skid system for the production of biodiesel.
Figure 8:
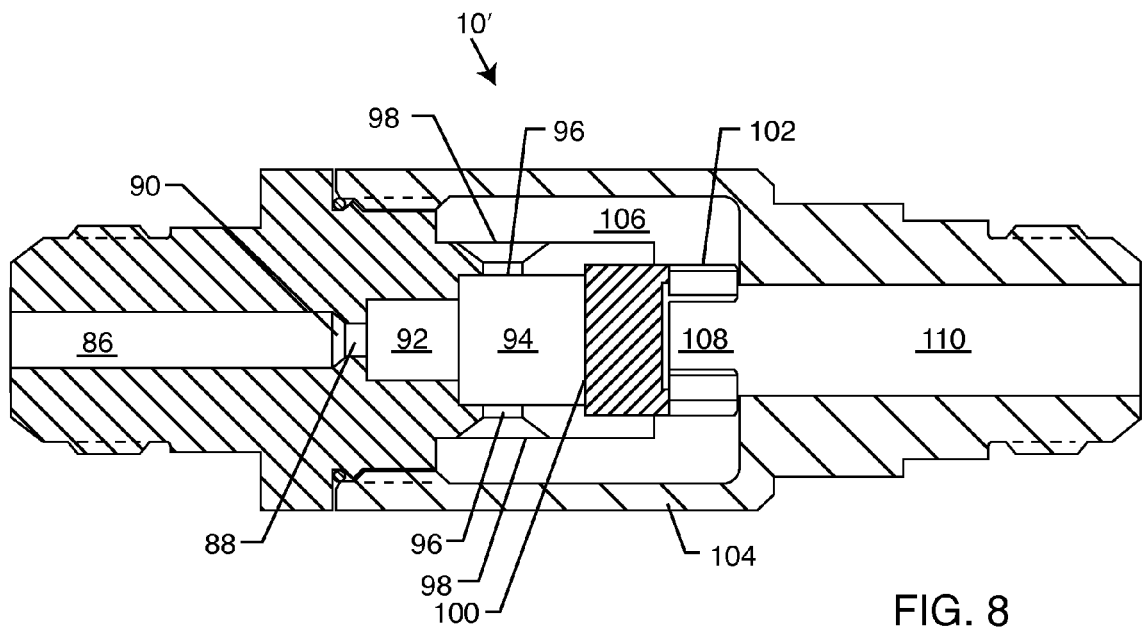
FIG. 8 is a cross-sectional view of an alternate embodiment of the cavitation device of the present invention.
Figure 9:
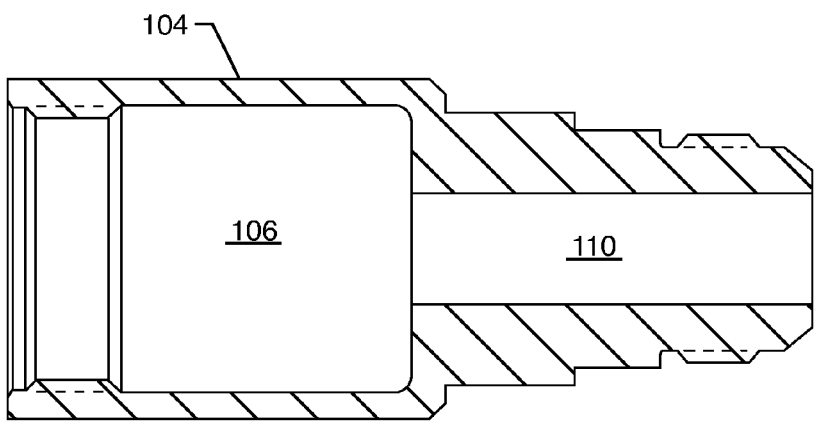
FIG. 9 is a cross-sectional view of an outlet portion of the cavitation device depicted in FIG. 8.
Figure 10:
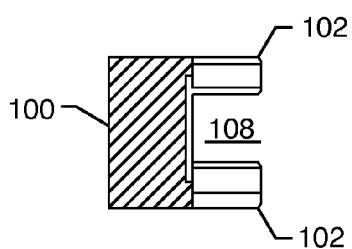
FIG. 10 is a side, cross-sectional view of the impact pad of the cavitation device of FIG. 8.
Figure 11:
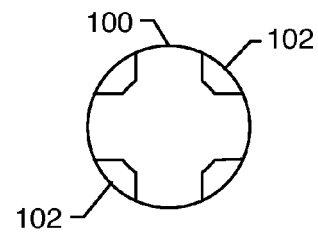
FIG. 11 is an end view of the impact pad of the cavitation device of FIG. 8.

FIG. 7 depicts schematically a skid unit 70 for producing biodiesel. The skid unit 70 is comprised of three pumps 72a, 74b, 72c for feeding oil 74a, alcohol 74b, and catalyst solution 74c; three mass flow meters 76a, 76b, 76c; two static mixers 78a, 78b; a high pressure pump 80; two cavitation devices 82a, 82b; and a vessel 84 to hold biodiesel product after the reaction. The cavitation devices 82a, 82b can be any of the embodiments 10, 10' described herein. The skid unit control panel and its back plate are enclosed in a metal box coated with a suitable paint, for example RAL Grey 2 Part Epoxy. The skid unit includes incidental equipment to complete the assembly such as, pressure relief valves, regulators, pulsation dampers, armored cables, stainless steel piping, manual valves (304 SS or comparable valves), flexible braided stainless steel hoses of varying diameter, a pressure transmitter 1500 PSIG or other, as required, XP rated 90 degree fittings, pressure gauges (preferably glycerol-filled), snubbers for pressure gauges, hydraulic fittings, check valves, flow control device, electrical terminal blocks, covers, Panduit® and the accessories required to interconnect the aforementioned parts. Such assembly requirements will be understood by those skilled in the art. The skid system 70 has an average capacity of 14,000-57,000 gallons per day with multiple feedstock (vegetable oil, beef tallow or yellow grease with up to 4.5% FFA) to produce biodiesel that meets ASTM standard requirements.

The present invention employs a specific process for creating hydrodynamic cavitation in fluids. The process involves flowing the fluid through the cavitation device 10 having a specified inlet flow velocity and system pressure through acceptable piping and pumping means. The inlet velocity and system pressure vary according to the reaction mixture properties. The preferred flow rate is approximately ten gallons per minute, but may be adjusted lower or higher according to output requirements without affecting the results of the cavitation process. The preferred system pressure is 25-5,000 psi. In a transesterification reaction, where the reagents are tallow (~2.5% FFA), methanol and sodium hydroxide, the preferred inlet velocity is ten gallons per minute and the preferred system pressure is about 500 psi.

Using the prior art processes discussed above, test quantities of fatty acid methyl and ethyl esters of five types of vegetable oils and animal fats were processed, characterized and ASTM performance tested. The vegetable oils and animal fats used as feedstocks for the fatty acid methyl and ethyl esters include: canola crude non-degummed oil with 3.2% FFA, rapeseed oil, soybean crude oil and soybean degummed oil (soybean oils with 1-1.4% FFA), and beef tallow (4.2% FFA). Vegetable oils were processed under ambient temperature and beef tallow was processed at a temperature 25-35° C. using the inventive cavitation device 10 and method with only one pass through, producing better end product when compared to the prior art processes.

The apparatus and method described herein, subject to the conditions and specifications of usage, provide a method for producing biodiesel. The processing is dependant upon the properties of the fluidic reaction mixture being processed and the energy requirements necessary to generate cavitation in the fluid.

The inventive method and cavitation device 10, 10' may be used in any combination of single-pass, multi-pass, parallel flow, series flow, or other variations of deployment to render the desired result. As this patent applies to the chemical and physical nature of the process occurring within cavitation device 10, 10', the patent also covers any array of deployment or fluid circuitry allowable by such device.

Thus, the disclosed method represents an advanced and highly optimized approach that allows completing transesterification by applying a single flow-through passage of the reaction medium through the hydrodynamic cavitation device. Apart from known methods, the proposed method's efficiency is not a function of the degree of mixing but rather a function of the unique gas-liquid reaction conditions allowing the high conversion rates and minimal residency time. The proposed process is based on the formation of short-lived gas bubbles comprised of methanol (ethanol and/or other low molecular weight alcohol), their subsequent growth, pulsation, and controlled implosions within the catalyst-enriched fatty acid triglyceride liquid phase. The alcohol-targeted cavitation is the cornerstone of the present process, which consists of generating cavitation by introducing the reaction mixture to a flow-through cavitation device provided with the sequential compartments of varying diameters and inner surface features, reducing the pressure of fluidic medium (reaction mixtures) such that it approaches the phase/liquid threshold of the alcohol, and conducting the cavitation such that there is the generation of alcohol vapor bubbles followed by their implosion in high-pressure zones.

The present process significantly differs from all other disclosed methods by supplying the unique, previously unknown reaction conditions for conducting the advanced gas-liquid esterification and transesterification processes. The method allows for shorter reaction time and high yield by creating optimal conditions required for the gas-liquid process to proceed to its completion. Since the transient gas phase is represented by the enormous number of short-lived alcohol vapor-filled micro bubbles distributed throughout the fluidic reaction mixture, the proposed method provides a very large interphase reaction surface, superior mixing and the prompt separation of reaction mixture into biodiesel and glycerol phases. The hydrodynamic cavitation-assisted gas-liquid transesterification is characterized with improved efficiency in comparison with other methods, such as injecting dry methanol gas in biolipid premixed with a catalyst or running the reaction at a temperature above the boiling point of methanol in an explosion-proof vessel.

The proposed cavitation device is particularly designed for mixing biolipids, low molecular weight alcohol, and catalyst and generating in this mixture the transient cavitation features followed by almost immediate, spontaneous separation of the reaction mixture comprised of the transesterification and/or esterification reaction products, residual initial reagents, catalyst, and by-products in biodiesel and glycerol layers. The layer containing most of the produced biodiesel is the upper one. The bottom layer contains glycerol, alcohol, and traces of other compounds. The separation can be improved by using centrifugation or other separation equipment, depending on equipment and energy cost and other considerations. It should be emphasized that the present cavitation device is optimized in such a way to drive the gas phase-liquid phase reaction while preventing the formation of inseparable emulsion, i.e., to allow the prompt and efficient separation of the synthesized biodiesel and glycerol. The flow-through hydrodynamic cavitation-assisted transesterification and/or esterification can be carried out in-line rather than using time-consuming batch processing. An industrial scale device may allow processing of thousands barrels per day.

Although several embodiments have been described in some detail for purposes of illustration, various modifications may be made without departing from the scope and spirit of the invention. Accordingly, the invention is not to be limited, except as by the appended claims.

What is claimed is:

1. A method for producing biodiesel from biolipids comprising the steps of:
    mixing said biolipids with a low-molecular weight alcohol and a catalyst to obtain a two phase, liquid-liquid fluidic reaction mixture;
    providing a flowpath through a hydrodynamic cavitation device;
    pumping the fluidic reaction mixture through a multi-jet nozzle in the flowpath, the multi-jet nozzle having a plurality of channels, wherein the multi-jet nozzle creates cavitation features in the fluidic reaction mixture;
    passing the fluidic reaction mixture through a plurality of spiral guides disposed in a working chamber in the flowpath, wherein the spiral guides create cavitation features in the fluidic reaction mixture;
    conveying the fluidic reaction mixture through a plurality of flow guides in a vortex chamber, wherein the flow guides and vortex chamber create cavitation features in the fluidic reaction mixture;
    reacting the biolipids with the low-molecular weight alcohol in each of the pumping, passing and conveying steps to produce the biodiesel and a glycerol; and
    separating the biodiesel from the glycerol.

2. The method of claim 1, wherein the pumping step comprises the steps of:
    generating an area of reduced fluid pressure in the fluidic reaction mixture resulting from being pumped through contractions in the plurality of channels causing an increase in fluid velocity, wherein the fluid pressure is reduced to at least a vapor pressure of the low-molecular weight alcohol;
    creating cavitation features, comprising cavitation vapor bubbles in the fluidic reaction mixture, the cavitation vapor bubbles containing low-molecular weight alcohol vapor resulting from the area of reduced fluid pressure, wherein the low-molecular weight alcohol forms a vapor at the reduced fluid pressure, to obtain a generally two-phase liquid-gas fluidic reaction mixture containing part of the biolipids in a liquid state and part of the low-molecular weight alcohol in a gaseous state;
    collapsing the cavitation vapor bubbles resulting in localized elevations of temperature and pressure; and
    forming microbubbles in the fluidic reaction mixture following collapse of the cavitation vapor bubbles.

3. The method of claim 1, wherein the passing step comprises the steps of:
    generating an area of reduced fluid pressure in the fluidic reaction mixture resulting from being passed through contractions created by the plurality of spiral guides in the working chamber causing an increase in fluid velocity, wherein the fluid pressure is reduced to at least a vapor pressure of the low-molecular weight alcohol;
    creating cavitation features, comprising cavitation vapor bubbles in the fluidic reaction mixture, the cavitation vapor bubbles containing low-molecular weight alcohol vapor resulting from the area of reduced fluid pressure, wherein the low-molecular weight alcohol forms a vapor at the reduced fluid pressure, to obtain a generally two-phase liquid-gas fluidic reaction mixture containing part of the biolipids in a liquid state and part of the low-molecular weight alcohol in a gaseous state;
    collapsing the cavitation vapor bubbles resulting in localized elevations of temperature and pressure; and
    forming microbubbles in the fluidic reaction mixture following collapse of the cavitation vapor bubbles.

4. The method of claim 1, wherein the conveying step comprises the steps of:
    generating an area of reduced fluid pressure in the fluidic reaction mixture resulting from being conveyed through contractions in the plurality of flow guides in the vortex chamber causing an increase in fluid velocity, wherein the fluid pressure is reduced to at least a vapor pressure of the low-molecular weight alcohol;
    creating cavitation features, comprising cavitation vapor bubbles in the fluidic reaction mixture, the cavitation vapor bubbles containing low-molecular weight alcohol vapor resulting from the area of reduced fluid pressure, wherein the low-molecular weight alcohol forms a vapor at the reduced fluid pressure, to obtain a generally two-phase liquid-gas fluidic reaction mixture containing part of the biolipids in a liquid state and part of the low-molecular weight alcohol in a gaseous state;
    collapsing the cavitation vapor bubbles resulting in localized elevations of temperature and pressure; and
    forming microbubbles in the fluidic reaction mixture following collapse of the cavitation vapor bubbles.

5. The method of claim 1, further comprising the step of introducing the fluidic reaction mixture to an atomizing cone which has an increasing cross-sectional area, wherein the fluidic reaction mixture loses all cavitation features.

6. The method of claim 1, providing a flowpath through a plurality of hydrodynamic cavitation devices and repeating the pumping, passing, conveying and reacting steps in each of the plurality of hydrodynamic cavitation devices.

7. The method of claim 1, wherein the catalyst comprises: an alkoxide, carbonate or hydroxide of sodium, potassium, calcium or barium; an inorganic base; an organic base; tetrabutylammonium tribromide (TBATB); hydrochloric acid; sulfuric acid; sulfonic acid; a heteropoly acid; a Lewis acid; a Brønsted acid; a Brønsted acidic ionic liquid; a membrane catalyst; acetyl chloride/ethanol; and/or lipase.

8. The method of claim 1, wherein the biodiesel comprises a fatty acid lower alkyl ester.

9. The method of claim 1, wherein the biolipids comprise: crude or preliminarily treated plant oil, including canola oil, castor bean oil, coconut oil, corn oil, cotton oil, hemp oil, jatropha oil, linseed (flax seed) oil, mustard seed oil, nut oil, olive oil, palm oil, peanut oil, rapeseed oil, safflower oil, soybean oil, sunflower oil, and tall oil; algal oil; fish oil; animal fat, including grease, lard, tallow and waste fat, bird fat; and any oil produced by using wild-type or genetically modified bacteria, yeast, fungi or other live unicellular or multicellular organisms.

10. The method of claim 1, wherein the low-molecular weight alcohol comprises a C1-C4 alcohol, methanol, ethanol, 1-propanol, 2-propanol, or 1-butanol.

11. The method of claim 1, wherein prior to the mixing step, further comprising the step of:
   adding a reagent to the biolipids and subjecting the biolipids and reagent to an initial hydrodynamic cavitation treatment.

* * * * *